United States Patent [19]

McGrath

[11] Patent Number: 5,360,932

[45] Date of Patent: Nov. 1, 1994

[54] PROCESS FOR REDUCING AROMATIC HALO-DINITRO-DIOLS IN THE PRESENCE OF HYDROGEN HALIDE

[75] Inventor: Patrick J. McGrath, Martinez, Calif.

[73] Assignee: The Dow Chemical Company, Midland, Mich.

[21] Appl. No.: 2,578

[22] Filed: Jan. 11, 1993

Related U.S. Application Data

[63] Continuation-in-part of Ser. No. 855,284, Mar. 23, 1992, abandoned.

[51] Int. Cl.$^5$ .............................................. C07C 209/36
[52] U.S. Cl. ........................................ 564/418; 564/423
[58] Field of Search ............................. 564/418, 423

[56] References Cited

U.S. PATENT DOCUMENTS

| | | | |
|---|---|---|---|
| 3,079,435 | 2/1963 | Freifelder | 260/562 |
| 4,766,244 | 10/1986 | Lysenko | 564/418 |
| 5,001,265 | 7/1989 | Liu et al. | 564/418 |

*Primary Examiner*—Glennon H. Hollrah
*Assistant Examiner*—Brian M. Burn

[57] ABSTRACT

An aromatic diamino-diol (such as 4,6-diaminoresorcinol) is made by reducing an aromatic halo-dinitro-diol (such as 2-halo-4,6-dinitroresorcinol) with molecular hydrogen in an aqueous mixture containing a noble metal hydrogenation catalyst, an aqueous solvent and about 2 moles of hydrogen halide per mole of aromatic halo-dinitro-diol, plus an additional quantity sufficient to provide a 0.75 to 4 molar solution of the hydrogen halide.

14 Claims, No Drawings

PROCESS FOR REDUCING AROMATIC HALO-DINITRO-DIOLS IN THE PRESENCE OF HYDROGEN HALIDE

CROSS-REFERENCE TO RELATED APPLICATION

This application is a continuation-in-part of the co-pending application Ser. No. 07/855,284, filed Mar. 23, 1992 (now abandoned).

BACKGROUND OF THE INVENTION

This invention relates to the art of synthesizing diaminobenzenediols and related compounds.

Metal catalyzed hydrogenation of halo-dinitro-dihydroxy benzenes such as 2-halo-4,6-dinitroresorcinol is known to be useful for synthesizing diaminobenzenediols, such as 4,6-diaminoresorcinol. See Lysenko, *High Purity Process for the Preparation of 4,6-Diamino-1,3-benzenediol*, U.S. Pat. No. 4,766,244 (Aug. 23, 1988) which is incorporated herein by reference. During hydrogenation, the nitro groups are converted to amine groups, and the halogen is removed from the aromatic ring as hydrogen halide.

At high pH, the selectivity of the reaction is diminished. The patent of Liu, U.S. Pat. No. 5,001,265 (Mar.19, 1991), which is incorporated herein by reference, shows that the reduction can be carried out in an aqueous solution that contains an acid that is weaker than a hydrogen halide but is strong enough to protonate and protect the aminophenol. That process is advantageous because it uses an aqueous solvent, but it has other drawbacks. It produces an aqueous waste stream that contains both hydrogen halide ions (from the halogen that is removed during hydrogenation) and other ions (such as phosphate ions) from the protective acid. Such mixed waste streams are more difficult to purify or recycle than streams containing a single ion.

What is needed is a method to reduce the halo-dinitro-benzenediol compound to an aromatic diaminodiol rapidly with high selectivity without putting a mixture of different ions into the waste stream.

SUMMARY OF THE INVENTION

The present invention is a process for synthesizing an aromatic diamino-diol compound said process comprising the step of contacting an aromatic halo-dinitro-diol compound with an excess of hydrogen in the presence of:

(1) a noble metal hydrogenation catalyst;
(2) an aqueous solvent; and
(3) about 2 to 6 moles of hydrogen halide per mole of aromatic halo-dinitro-diol plus an additional amount sufficient to provide about a 0.75 to 4 molar solution of hydrogen halide in the aqueous solvent, under conditions such that an aromatic diaminodiol compound is formed.

The process of the present invention eliminates or minimizes organic solvents and produces an aqueous waste stream that contains only hydrogen halide ions. The compounds that are made are useful as intermediates in the synthesis of dyes and pharmaceuticals; as photographic developers, as described in 2 Encyclopedia Chem. Tech. - 3rd Ed., *Aminophenols*, 422–40 (J. Wiley & Sons 1978); and as co-monomers for synthesizing polybenzoxazole (PBO) polymers, as described in 11 Ency. Poly. Sci. & Tech., *Polybenzothiazoles and Polybenzoxazoles* 601 (1988), which are incorporated herein by reference.

DETAILED DESCRIPTION OF THE INVENTION

The process of the present invention utilizes the catalytic hydrogenation of an aromatic halo-dinitro-diol. (For purposes of brevity, the aromatic halo-dinitro-diol shall be referred to hereafter as the "starting compound") The starting compound comprises an aromatic ring bonded to a halogen atom, two hydroxy groups and two nitro groups. Each nitro group is preferably ortho to a different hydroxy group.

Both hydroxy groups are preferably ortho to the halogen atom. The halogen bonded to the aromatic ring is preferably chlorine, bromine or iodine and more preferably chlorine.

The aromatic ring may be heterocyclic, such as pyridine, but is preferably carbocyclic. The aromatic ring may have substituents other than the hydroxy, nitro and halogen substituents previously described, which are stable under reaction conditions and do not interfere with the reaction. Examples of other substituents include a second halogen atom a phenyl moiety, a phenoxy moiety, an alkoxy moiety and a lower (about 1–6 carbon) alkyl moiety. The aromatic ring most preferably has no substituents other than those specifically identified.

The starting compounds preferably comply with formula 1(a):

and more preferably comply with either formula 1(b) or 1(c):

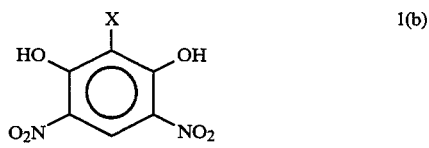

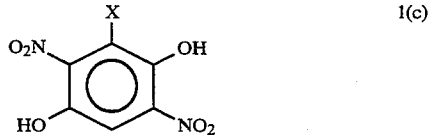

wherein Ar and X have the meaning and preferred embodiments previously given. The most preferred formula is formula 2(b). Examples of suitable starting compounds include 2,5-dinitro-3-halohydroquinone and 2-halo-4,6-dinitroresorcinol. More preferred examples of suitable starting compounds include 4,6-dinitro-2-chlororesorcinol; 4,6-dinitro-2-bromoresorcinol; and 2,5-dinitro-3-chlorohydroquinone.

Starting compounds can be synthesized by obvious substitution of reagents into known processes. For instance, they may be synthesized by nitrating an appropriate aromatic di- or trihalide, followed by displacement of one or more halogen atoms with hydroxy groups as described in U.S. Pat. No. 4,766,244, which is incorporated herein by reference.

The starting compound is contacted with molecular hydrogen. The hydrogen is preferably present in a stoichiometric excess over the amount of starting compound. Excess hydrogen is desirable because hydrogen protects the catalyst from attack by the hydrogen halide. However, the hydrogen must be on the catalyst surface to protect the catalyst. In a reduction reactor, the designed rate rate of hydrogen mass transfer is preferably greater than the rate of reduction. Therefore, it is preferable to maintain a hydrogen rich environment around the catalyst. Optimum conditions for this will vary depending upon equipment and reduction chemistry being practiced. Persons of ordinary skill in the art can readily find suitable conditions for maintaining a hydrogen rich environment by optimizing the partial pressure of hydrogen in the reactor, reactor mixing, and the catalyst loading of the system.

The contact is made in an aqueous solvent. (The term "solvent" does not necessarily imply that the aqueous solvent dissolves large quantities of the starting compound or the hydrogen. The starting compound frequently forms a slurry in water.)

The amount of solvent should be sufficient to entrain enough hydrogen for a reasonable rate of reaction and to leave the slurry reasonably stirrable. The maximum amount of solvent is governed primarily by practical considerations. At higher ratios of water to starting compound, the capacity of batch-type reaction equipment is necessarily lower. The best ratio of starting compound to solvent varies depending upon the temperature, the concentration of hydrogen halide in the reaction and the reactor configuration. The concentration of starting compound in the solvent is preferably no more than about 2.0 mole per liter, more preferably no more than about 1.5 mole per liter and most preferably no more than about 1.0 mole per liter. The bulk concentration of starting compound in the solvent is preferably no less than about 0.01 mole per liter and most preferably no less than about 0.5 mole per liter.

The aqueous solvent may be mixed with organic diluents, such as alkanols and glycols, which are miscible with water. The term "organic diluent" does not refer to the starting compound, but only to organic compounds which function as solvents. The organic diluent preferably makes up a small enough part of the solution to minimize the flame hazard resulting from its presence. The organic diluent should make up no more than 50 percent of the solvent by weight, preferably no more than 25 percent and more preferably no more than 10 percent. The solvent most preferably contains essentially no organic diluent, such that water is the only solvent.

The reaction takes place in the presence of a noble metal hydrogenation catalyst. Suitable noble metals are those known to promote both hydrogenation of nitro groups and hydrogenation of aromatic halides to form aromatic rings and hydrogen halide. Examples of suitable noble metals include gold, silver, platinum, palladium, iridium, rhodium, mercury, ruthenium and osmium. Preferred metals are platinum and palladium and the most preferred metal is palladium. The catalyst metal may be used in any form which is suitable to catalyze the reaction. The catalyst may be used unsupported, but is preferably supported by a support, such as carbon or silica-alumina powder or a zeolite. Catalysts that contain palladium supported on silica-alumina powder preferably contain at least about 0.05 weight percent palladium and more preferably at least about 5 weight percent palladium. They preferably contain no more than about 25 weight percent palladium, and more preferably no more than about 10 weight percent.

The amount of catalyst used is governed essentially by practical considerations which are familiar to persons of ordinary skill in the art. When the catalyst is a supported palladium catalyst, the reaction mixture preferably contains at least about 0.0001 moles of palladium per mole of starting compound, and more preferably contains at least about 0.01 moles of palladium per mole of starting compound. The reaction mixture preferably contains no more than about 0.25 moles of palladium per mole of starting compound, and more preferably contains no more than about 0.04 moles of palladium per mole of starting compound.

The reaction takes place in the presence of a hydrogen halide. The halogen is preferably chlorine, bromine or iodine. It is more preferably chlorine or bromine, and it is most preferably chlorine. The halogen in the hydrogen halide and the halogen in the starting compound are preferably the same.

The reaction mixture may also contain other suitable acids, such as the acids described in Col. 4 of Liu U.S. Pat. No. 5,001,265 (Mar. 19, 1991), which is incorporated herein by reference. However, the presence of other acids will add different ions to the waste stream and defeat a principle advantage in the invention. The reaction preferably contains no acid other than hydrogen halide.

The reaction mixture should contain at least 2 moles of hydrogen halide per mole of starting compound, plus enough additional hydrogen halide to make about a 0.75 molar concentration of the hydrogen halide in the solvent. The concentration of additional hydrogen halide in the solvent is no more than about 4 molar, preferably no more than about 3 molar, more preferably no more than about 2 molar and most preferably no more than about 1 molar. Too little hydrogen halide usually lowers the selectivity of the reaction, whereas too much hydrogen halide lowers the speed of the dechlorination reaction at a given temperature. Moreover, too much hydrogen halide may cause the product to precipitate in a mixture with the catalysts so that an additional separation procedure is necessary.

The hydrogen may be introduced into the slurry by any means effective to achieve a reasonable dispersion. For instances it may be sparged into the slurry or introduced into the headspace and dispersed with an entrainment agitator. Good mixing is important to maintain an even dispersion of reagents throughout the system and adequate access of hydrogen to the catalyst.

The temperature of the reaction may be any at which the reaction proceeds and the reagents and products are stable. The reaction may be carried out in a single step or in two stages: a lower temperature reduction of the nitro groups followed by a higher temperature hydrodechlorination reaction. The lower temperature step is preferably carried out at temperatures as low as about $-15°$ C. to $40°$ C. The maximum temperature achieved during the hydrodechlorination reaction is preferably at least about $50°$ C. and most preferably at least about $80°$ C. The maximum temperature of the reaction is preferably no more than the boiling point of the solvent under reaction conditions. In most cases, it is preferably at most about $110°$ C. and more preferably at most about $100°$ C. The reaction usually proceeds more rapidly at higher temperatures. The reaction should be carried out in a reducing atmosphere.

Catalyst is preferably removed from the reaction mixture by known means such as filtration.

The product of the reaction contains an aromatic ring, two hydroxyl groups bonded to the aromatic ring in the same positions as the hydroxy groups on the starting compound, two primary amine groups bonded to the aromatic ring in the positions formerly occupied by the nitro groups on the starting compound, and a hydrogen in each position formerly occupied by a halogen atom. The product is susceptible to air oxidation while in solution or as a wet solid. The product is preferably precipitated from solution and dried as soon as possible. The product in solution is preferably protonated. The precipitated product is more stable with respect to air oxidation if it is precipitated as an acid salt. Precipitation can be accomplished by known methods, such as cooling the solution, adding a non-solvent, or acidification of the solution. Examples of suitable non-solvents include alkanols such as methanol, ethanol and propanol.

The selectivity of product recovered is preferably greater than 90 percent, more preferably at least about 95 percent, and most preferably at least 98 percent based upon the starting compound.

Compounds produced by the present invention can be used as described in the references previously cited and incorporated by reference.

ILLUSTRATIVE EMBODIMENTS

The following examples are for illustrative purposes only and should not be taken as limiting either the specification or the claims. Unless stated otherwise, all parts and percentages are given by weight.

EXAMPLE 1-Reduction of 2-chloro-4,6-dinitroresorcinol

A stirred reactor is charged with:
(a) 185 g of a mixture containing about 70 weight percent 2-chloro-4,6-dinitroresorcinol and about 30 weight percent water;
(b) 201.6 g of 36.5 weight percent aqueous HCl solution;
(c) 872.41 g of water; and
(d) 57.26 g of 5 percent palladium on silica-alumina powder catalyst.

Excess hydrogen is introduced into the reactor. The reaction is continued with agitation for 200 minutes at 25° C., for 340 minutes as the temperature increases from 25° C. to 75° C., and for 135 minutes at 75° C. A 4.7 mole quantity of molecular hydrogen is used in the reaction. The reaction mixture is filtered and mixed with concentrated (36 percent) HCl that contains 10 g of tin (II) chloride to precipitate the product. A 66.5 g quantity of 4,6-diaminoresorcinol dihydrochloride is recovered and characterized by liquid chromatography.

What is claimed is:

1. A process for synthesizing an aromatic diamino-diol compound, said process comprising the step of contacting an aromatic halo-dinitro-diol compound with an excess of hydrogen in the presence of:
(1) a noble metal hydrogenation catalyst;
(2) an aqueous solvent; and
(3) about 2 moles of hydrogen halide per mole of aromatic halo-dinitro-diol plus an additional amount sufficient to provide about a 0.75 to 4 molar solution of hydrogen halide in the aqueous solvent, under mixing under conditions such that an aromatic diamino-diol is formed.

2. The process of claim 1 wherein the catalyst contains palladium.

3. The process of claim 1 wherein the hydrogen halide is hydrogen chloride.

4. The process of claim 1 wherein the temperature is between about −15° C. and about 110° C.

5. The process of claim 1 wherein the reaction mixture contains no more than about 1 molar concentration of hydrogen halide, in addition to 2 moles of hydrogen halide per mole of aromatic halo-dinitrodiol.

6. The process of claim 1 wherein the solvent contains essentially no organic diluent.

7. The process of claim 1 wherein the aromatic halo-dinitro-diol compound is any one of:

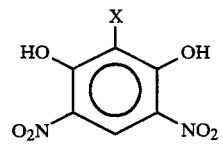

2(b)

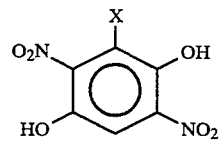

2(c)

wherein X is a halogen atom.

8. The process of claim 1 wherein the aromatic halo-dinitro-diol compound is 2-chloro-4,6-dinitroresorcinol.

9. A process for making a 4,6-diaminoresorcinol, comprising the step of contacting a 2-halo-4,6-dinitroresorcinol with excess hydrogen in the presence of
(a) a noble metal hydrogenation catalyst;
(b) water; and
(c) about 2 moles of hydrogen halide per mole of 2-halo-4,6dinitroresorcinol, plus an additional quantity of hydrogen halide sufficient to provide about a 0.75 to 2 molar solution,
under conditions such that the 4,6-diaminoresorcinol is formed.

10. The process of claim 9 wherein the temperature is between about −15° C. and about 110° C.

11. The process of claim 10 wherein the halogen in the 2-halo-4,6-dinitroresorcinol and the hydrogen halide is chlorine.

12. The process of claim 11 wherein the catalyst contains platinum or palladium.

13. The process of claim 12 wherein the catalyst contains palladium.

14. The process of claim 13 wherein the temperature is at least about 80° C.

* * * * *